US00PP24031P3

(12) United States Plant Patent
Li

(10) Patent No.: US PP24,031 P3
(45) Date of Patent: Nov. 19, 2013

(54) ***VERBENA* PLANT NAMED 'KLEVP11419'**

(50) Latin Name: *Verbena×hybrida*
Varietal Denomination: KLEVP11419

(75) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 73 days.

(21) Appl. No.: 13/506,018

(22) Filed: Mar. 21, 2012

(65) Prior Publication Data

US 2013/0254950 P1 Sep. 26, 2013

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new variety of *Verbena* named 'KLEVP11419', particularly characterized by having good flower quality, good branching, and flowers with large white eyes, is disclosed.

1 Drawing Sheet

Genus and species: *Verbena×hybrida.*
Variety denomination: 'KLEVP11419'.

BACKGROUND OF THE NEW PLANT

The present invention comprises a new and distinct variety of *Verbena*, botanically known as *Verbena×hybrida*, and hereinafter referred to by the variety name 'KLEVP11419'. The new variety is the result of a cross conducted in April 2008 in Cobbity, New South Wales, Australia between female *Verbena* plant, '1S109' (unpatented), and male *Verbena* plant, 'V 842' (unpatented). A single plant selection was subsequently chosen for further evaluation and asexual propagation.

The new variety was first propagated in January 2009 in Cobbity, New South Wales, Australia and has been asexually reproduced repeatedly by vegetative cuttings for three to four generations. 'KLEVP11419' has been found to retain its distinctive characteristics through successive asexual propagations.

Plant Breeder's Rights for this variety were applied for in Canada on Jan. 18, 2012. 'KLEVP11419' has not been made publicly available more than one year prior to filing of this application.

SUMMARY OF THE INVENTION

The following are the most outstanding and distinguishing characteristics of this new variety when grown under normal horticultural practices in a greenhouse in Sydney, Australia.

1. Good flower quality;
2. Large white eye; and
3. Good branching.

DESCRIPTION OF THE PHOTOGRAPH

This new *Verbena* plant is illustrated by the accompanying photograph which shows inflorescences of the plant. The colors shown are as true as can be reasonably obtained by conventional photographic procedures. The photograph is of a plant about 3 months old, taken in spring 2011, grown from a rooted cutting in a glass greenhouse in Stuttgart, Germany under normal horticultural practices.

DESCRIPTION OF THE NEW VARIETY

The following detailed descriptions set forth the distinctive characteristics of 'KLEVP11419'. The data which define these characteristics were collected from asexual reproductions carried out in Stuttgart, Germany. The plant history was taken in spring 2011 on 3-month old plants grown in 12 centimeter pots in a glass greenhouse with a minimum pinch date of 10 weeks. The color readings were determined under natural light. Color references are to The R.H.S. Colour Chart of The Royal Horticultural Society of London (R.H.S.), Fifth Edition (2007).

DESCRIPTION OF THE NEW PLANT

Classification:
- *Family.*—Verbenaceae.
- *Genus and species.—Verbena×hybrida.*
- *Common name.—Verbena.*
- *Denomination.*—'KLEVP11419'.

Parentage:
- *Female parent.—Verbena* plant, '1S109' (unpatented).
- *Male parent.—Verbena* plant, 'V 842' (unpatented).

Plant:
- *Form.*—Semi-trailing.
- *Growth and branching habit.*—Freely branching.
- *Height (from top of soil).*—Approximately 15.0 cm.
- *Width (horizontal plant diameter).*—Approximately 45.0 cm.
- *Time to produce a finished flowering plant.*—Approximately 9 weeks.
- *Time to initiate and develop roots.*—4 weeks.
- *Root description.*—Fine, RHS 155B.

Stems:
- *Number of branches per plant.*—Approximately 25.
- *Length.*—Approximately 20.0 cm.

*Diameter per branch* (*measured from the midpoint*).—15.0 mm.
*Internode length.*—3.0 cm.
*Color.*—RHS 133D.
*Anthocyanin.*—Absent.
*Texture and appearance.*—Short pubescence.

Leaves:
*Arrangement.*—Opposite.
*Color.*—Immature leaf (both surfaces): RHS 141A. Mature leaf (both surfaces): RHS 139C.
*Length.*—3.0 cm.
*Width.*—2.0 cm.
*Shape.*—Elliptic.
*Apex.*—Cuspidate.
*Base.*—Closed.
*Margin.*—Serrated.
*Texture* (*both surfaces*).—Leathery.
*Venation pattern.*—Palmate.
*Venation color.*—RHS 141A.
*Petioles.*—Length: 0.5 cm. Diameter: Less than 0.2 cm. Color: RHS 141A. Texture: Rough.

Flower buds:
*Shape.*—Tall cylinder.
*Length.*—1.0 cm.
*Diameter.*—Less than 0.2 cm.
*Color* (*at tight bud*).—RHS 141D.

Inflorescence:
*Blooming habit* (*flowering season*).—From early spring to late fall in central Europe.
*Lastingness of individual blooms on the plant.*—2 weeks.
*Fragrance.*—Absent.
*Inflorescence type.*—Umbel.
*Length of inflorescence.*—5.0 cm.
*Diameter of inflorescence.*—6.0 cm.
*Number of florets per inflorescence.*—Approximately 25.
*Peduncle.*—Length: 4.0 cm. Diameter: Less than 0.1 cm. Color: RHS 141A. Texture: Rough.

Florets:
*Form.*—Tall cylinder, opening at the end.
*Length.*—2.0 cm.
*Diameter.*—0.2 cm at the bottom, 0.2 cm at the top.
*Color.*—Immature and mature flowers (both surfaces): RHS 41A.
*Corolla tube length.*—0.2 cm.
*Corolla tube color.*—RHS 141A.
*Petals.*—Length of lobe: 1.5 cm. Diameter of lobe: 2.0 cm. Lobe shape: Reniform. Apex: Obtuse. Base: Closed. Margin: Entire.
*Pedicels.*—Length: 3.0 cm. Diameter: 2.0 mm. Color: RHS 141A. Texture and appearance: Smooth and satiny.

Calyx:
*Arrangement.*—Round.
*Sepals.*—Shape: Funnel. Length: 2.0 cm. Diameter: 0.2 cm. Color: RHS 141A. Apex: Wide open. Base: Open. Margin: Satiny. Texture: Smooth.

Reproductive organs:
*Stamens.*—Quantity: 5. Color: RHS 155D. Filament length: 0.5 cm. Filament diameter: Less than 0.1 cm.
*Anther.*—Shape: Fused. Color: RHS 155D. Length: 0.2 cm. Diameter: Less than 0.1 cm.
*Pollen.*—Quantity: Sparse. Color: RHS 7C.
*Pistils.*—Quantity: 2. Length: Less than 0.1 cm. Diameter: Less than 0.1 cm. Stigma: Color: RHS 155C. Shape: Lanceolate. Length: Less than 0.5 cm. Diameter: Less than 0.1 cm. Style: Color: RHS 155C. Length: Less than 0.3 cm. Diameter: Less than 0.1 cm.

Fruit and seed set: None observed.

Disease, insect resistance, and physiological stress: Resistant to powdery mildew.

COMPARISON WITH PARENTAL AND COMMERCIAL VARIETIES

'KLEVP11419' differs from the female parent, *Verbena* plant '1S109' (unpatented), in that 'KLEVP11419' has better flower quality and better branching than than '1S109'.

'KLEVP11419' differs from the male parent, *Verbena* plant 'V 842', in that 'KLEVP11419' has a brighter flower color than 'V 842'.

'KLEVP11419' differs from the commercial variety, 'Empress Strawberry Charme' (patent status unknown), in that 'KLEVP11419' has a darker flower color with a more intense and larger white eye, while 'Empress Strawberry Charme' has a lighter flower color.

I claim:

1. A new and distinct variety of *Verbena* plant named 'KLEVP11419' as shown and described herein.

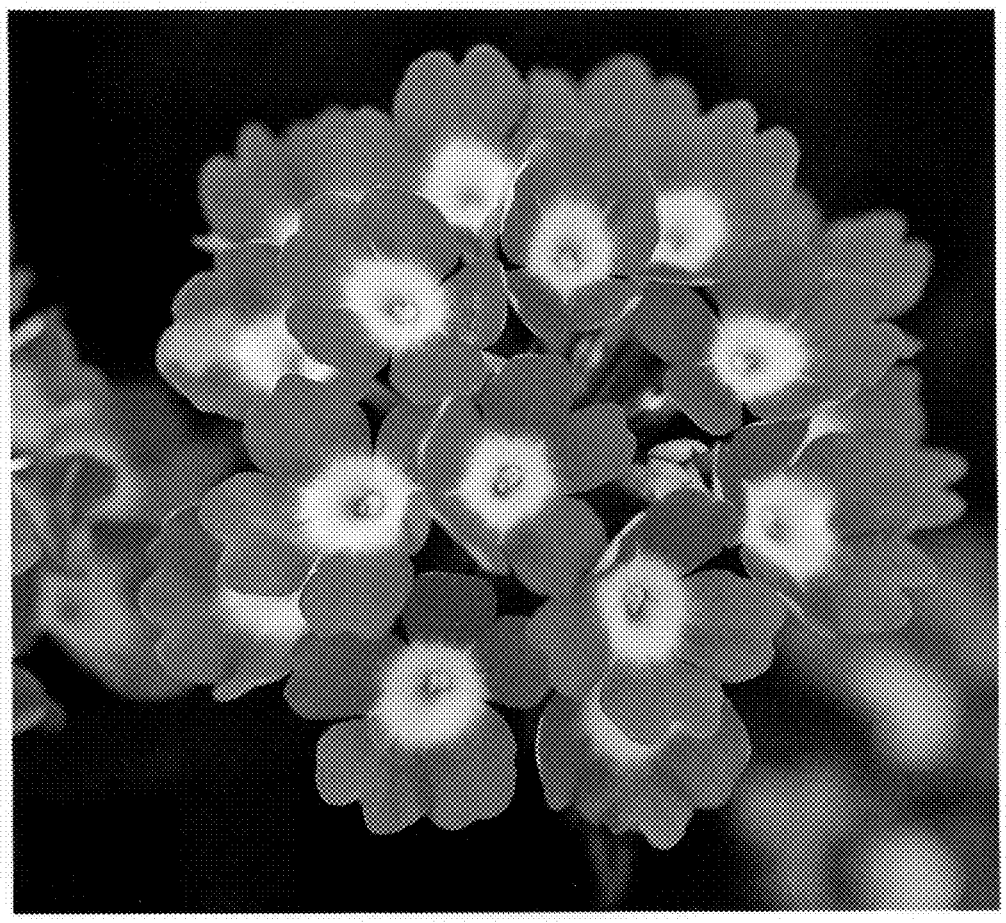

* * * * *